US008388699B2

(12) United States Patent
Wood et al.

(10) Patent No.: US 8,388,699 B2
(45) Date of Patent: Mar. 5, 2013

(54) METHOD FOR LEVELLING HAIR COLOUR

(75) Inventors: Jonathan Wood, Weinheim (DE);
Martin Uellner, Darmstadt (DE);
Mustafa Grit, Gernsheim (DE)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/384,940

(22) PCT Filed: Jul. 15, 2010

(86) PCT No.: PCT/EP2010/004321
§ 371 (c)(1),
(2), (4) Date: Jan. 19, 2012

(87) PCT Pub. No.: WO2011/018145
PCT Pub. Date: Feb. 17, 2011

(65) Prior Publication Data
US 2012/0132226 A1    May 31, 2012

(30) Foreign Application Priority Data

Jul. 22, 2009    (EP) .................................... 09009461

(51) Int. Cl.
*A61Q 5/10* (2006.01)
(52) U.S. Cl. ............. 8/405; 8/431; 424/70.16; 132/202; 132/208
(58) Field of Classification Search .............. 8/405, 431; 424/70.16; 132/202, 208
See application file for complete search history.

(56) References Cited

U.S. PATENT DOCUMENTS

| | | | |
|---|---|---|---|
| 3,590,122 | A | 6/1971 | Roberts et al. |
| 4,486,328 | A | 12/1984 | Knott et al. |
| 5,221,286 | A | 6/1993 | Singleton et al. |
| 5,431,698 | A | 7/1995 | Tennigkeit et al. |
| 5,683,474 | A | 11/1997 | Cotteret et al. |
| 5,785,961 | A | 7/1998 | Nakama et al. |
| 5,814,106 | A | 9/1998 | Audousset |
| 6,254,647 | B1 | 7/2001 | Fröhling |
| 6,312,677 | B1 | 11/2001 | Millequant et al. |
| 8,002,848 | B2 | 8/2011 | Miyabe |
| 8,021,439 | B2 | 9/2011 | Miyabe et al. |
| 2004/0133995 | A1 | 7/2004 | Cottard et al. |
| 2007/0157399 | A1* | 7/2007 | Nobuto et al. ..................... 8/405 |
| 2007/0169286 | A1 | 7/2007 | Narasimhan et al. |

FOREIGN PATENT DOCUMENTS

| | | |
|---|---|---|
| DE | 2432614 A1 | 1/1976 |
| DE | 102007048140 A1 | 4/2009 |
| EP | 524 612 A | 1/1993 |
| EP | 640 643 A | 3/1995 |
| EP | 0744175 A2 | 11/1996 |
| EP | 0925775 A2 | 6/1999 |
| EP | 0938888 A2 | 9/1999 |
| EP | 1036556 A2 | 9/2000 |
| EP | 1123693 A2 | 8/2001 |
| EP | 1219285 A2 | 7/2002 |
| EP | 1 470 812 A | 10/2004 |
| EP | 1411885 B1 | 5/2007 |
| EP | 1803436 A1 | 7/2007 |
| EP | 1982691 A1 | 10/2008 |
| EP | 2 062 562 A | 5/2009 |
| FR | 2920090 A1 | 2/2009 |
| GB | 1083007 A | 9/1967 |
| GB | 2 188 948 A | 10/1987 |
| JP | 50 005539 | 1/1975 |
| JP | 62185008 A | 8/1987 |
| JP | 63174917 A | 7/1988 |
| JP | 5286831 | 11/1993 |
| JP | 2003206221 | 7/2003 |
| WO | 95/15144 | 6/1995 |
| WO | 01/85113 A | 11/2001 |
| WO | 2002074271 A1 | 9/2002 |
| WO | 2005/065632 A1 | 7/2005 |
| WO | 2009047022 A1 | 4/2009 |
| WO | 2009054147 A1 | 4/2009 |
| WO | 2009054148 A1 | 4/2009 |

OTHER PUBLICATIONS

Nanho, Yukio et al., "Preparation of acidic permanent oxidative hair dyes," Chemical Abstracts, vol. 54, No. 2, Aug. 13, 1987 (abstract).
International Search Report for Related PCT/EP2010/004003, Mailed Mar. 16, 2011.
International Serach Report for Related PCT/EP2010/004004, Mailed Mar. 25, 2011.
International Search Report for Related PCT/EP2010/004005, Mailed Feb. 25, 2011.
International Search Report for Related PCT/EP2010/004006, Mailed Dec. 17, 2010.
International Search Report for Related PCT/EP2010/004007, Mailed Mar. 2, 2012. International Search Report for Related PCT/EP2010/004321, Mailed Mar. 16, 2011.
International Search Report for Related PCT/EP2010/004322, Mailed Jan. 24, 2012.
International Search Report for Related PCT/EP2010/004323, Mailed May 3, 2012.
International Search Report for Related PCT/EP2010/004324, Mailed Jan. 24, 2012.
International Search Report for Related PCT/EP2010/004325, Mailed Oct. 29, 2010.
Stic Search Report for Related U.S. Appl. No. 13/382,788, Dated Apr. 28, 2012.

\* cited by examiner

*Primary Examiner* — Eisa Elhilo
(74) *Attorney, Agent, or Firm* — Norris McLaughlin & Marcus, P.A.

(57) ABSTRACT

A method levels hair color, especially lighter colored hair or including lightened streaks or bleached streaks or bleached as a whole and after certain period of time contrast—difference in color—between the re-growth and formerly lightened parts is clearly visible. The method comprises at least two parts wherein one part being the part not closer to scalp which is artificially color changed to a lighter color by means of lightening and/or coloring and/or bleaching than the other part closer to scalp which is preferably undamaged and has its natural color, wherein hair is optionally shampooed and optionally towel dried and the part directly at the scalp, preferably undamaged and preferably has its natural color, is applied a composition resulting from mixing two compositions, A and B, prior to application.

14 Claims, No Drawings

METHOD FOR LEVELLING HAIR COLOUR

This application is a 371 application of PCT/EP2010/004321 filed Jul. 15, 2010, which claims foreign priority benefit under 35 U.S.C. §119 of European Application No. 09009461.6 filed Jul. 22, 2009.

The present invention relates to a method of levelling hair colour, especially lighter coloured hair or including lightened streaks or bleached streaks or bleached as a whole and after certain period of time contrast—difference in colour—between the re-growth and formerly lightened parts is clearly visible.

Making streaks, lightening and bleaching are commonly used hair dressing practices. The aim of such hair dressing services is to get lighter coloured hair parts, or colouring hair to a lighter shade and finally bleaching hair—taking away hair colour as a whole—in order to give attractive appearance. In practice, immediately after such service, consumers' hair has very attractive appearance and naturalness, but this lasts only for a limited period of time because of unattractive contrast between the re-growth and lighter coloured and/or lightened parts by means of bleaching becomes clearly visible. This is especially problem when the uncoloured natural hair is considerably darker, i.e. re-growth has a considerably darker colour than the lighter coloured parts. Colour difference does reduce attractiveness and naturalness and it is highly desirable to give hair attractive colour appearance again without extensive additional chemical treatments. Especially, since such correction is often needed in a relatively short period of time after previous chemical treatment, the corrective treatment must not take a long time, preferably must easily be combinable with other type of hair dressing services, such as and preferably not involving any further chemical treatment. In other words, the corrective treatment should not cause any further damage to the hair or the damage caused by such service should be negligible compared to the damage caused by the previous colouring and/or bleaching.

After a long discussion with hair dressers and the end-user groups, the needs have been clearly identified of such a service. On these bases, various ways have been practiced and surprisingly found out that a levelling service combined with any hair care service is especially suited and it is easily applicable in any hair dressing salons.

It has further been identified that with the existing products and/or compositions, might be thought suitable for levelling hair colour, cause often dermatological incompatibilities with scalp such as itchiness, redness and scaling reported by volunteers.

Therefore, present invention starts from the problems of effective and easy applicable levelling service wherein the compositions and/or mixtures used for this purpose are mild to skin and do not cause any dermatological incompatibilities.

The inventors of the present invention have surprisingly found out that an aqueous composition resulting from mixing two compositions A and B wherein A is an acidic composition and comprises at least one oxidizing agent and B is an alkaline composition, applied onto hair as foam from a non-aerosol foamer vessel is perfectly suited for levelling hair colour. It as observed that the application is much easier, quicker, more even, and therefore the levelling effect is much more homogeneous compared to levelling effect achieved using bowl and brush application method.

Thus, the object of the present invention is a method of levelling colour of hair comprising at least two parts wherein one part being the part not closer to scalp which is artificially colour changed to a lighter colour by means of lightening and/or colouring and/or bleaching than the other part closer to scalp which is preferably undamaged and has its natural colour, wherein hair is optionally shampooed and optionally towel dried and the part directly at the scalp, preferably undamaged and preferably having its natural colour, is applied a composition resulting from mixing two compositions, A and B, prior to application, compositions A is an aqueous composition and comprises at least one oxidizing agent and has an acidic pH, preferably between 2 and 5 and composition B is an aqueous alkaline composition having a pH between 8 and 12, wherein composition A and/or B comprises at least one surfactant selected from non-ionic, anionic, amphoteric, cationic or cationizable ones, form a non-aerosol foamer vessel in the form of a foam and processed for up to 10 min, preferably between 1 and 8 min, more preferably between 2 and 7 min and most preferably between 2 and 5 min (all values are included) at a temperature between 20 and 45° C., preferably at an ambient temperature and rinsed off from hair and hair is optionally dried.

Further object of the present invention is to use of the above method for levelling hair colour.

With the term "levelling" it is meant that hair colour is made more uniform, if not equal, among the parts, preferably between two parts, having different colours wherein one part is artificially colour changed to a lighter colour than its natural colour by means of colouring and/or lightening and/or bleaching either as a whole or only in streaks which is not closer to the scalp and the other part which is closer to the scalp and being undamaged and having darker and preferably natural colour than the remaining part of the hair.

With the phrase "being not closer to the scalp" it is meant the part of hair towards to the tips.

With the phrase "being closer to the scalp" it is meant the hair that has grown since the previous colouration (re-growth) and it is between scalp and colour changed part.

It should be noted that the method of the present invention is certainly suitable for levelling colour of sun-lightened hair, especially seasonally, and/or age-darkened hair as well.

Composition B comprises at least one alkalizing agent. Suitable ones are ammonia (including ammonium hydroxide), carbonate and bicarbonate salts and a substituted amine compound according to general formula

wherein $R_1$, $R_2$ and $R_3$ are same or different H, $C_1$-$C_6$ alkyl, $C_1$-$C_6$ monohydroxyalkyl or $C_2$-$C_6$ polyhydroxyalkyl with the condition that at least one of $R_1$, $R_2$ and $R_3$ is a mono or polyhydroxyalkyl.

Suitable alkanolamines according to the general formula above are monoethanolamine, diethanolamine, triethanolamine, monoethanol methylamine, monoethanoldimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine.

Concentration of the ammonia or the amine compound according to the general formula above is dependent on the concentration of the fatty acid and also dependent on the alkalinity value targeted. In general it varies between 1 and 20%, preferably 1 and 15, more preferably 1 and 12.5 and most preferably 1 to 10% by weight calculated to the total of composition B.

Composition A and/or B comprises one or more surfactants selected from non-ionic, anionic, amphoteric and cationic or cationizable ones. Concentration of one or more surfactants is in the range between 0.5 and 15%, preferably between 1 and 12.5% and more preferably between 1 and 10% and most preferably between 2 and 7.5% by weight calculated to total of composition A or B.

Suitable non-ionic surfactants are alkyl polyglucosides of the general formula

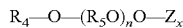

wherein $R_4$ is an alkyl group with 8 to 18 carbon atoms, $R_5$ is an ethylene or propylene group, Z is a saccharide group with 5 to 6 carbon atoms, n is a number from 0 to 10 and x is a number between 1 and 5. Examples are decyl glucoside, carpylyl glucoside, ceteary glucoside, cocoyl ethyl glucoside, lauryl glucoside, myristyl glucoside and coco glucoside. Preferred are decyl glucoside and coco glucoside which are commericially available with the trade name Plantacare from the company Cognis.

Further non-ionic surfactants suitable are long-chain fatty acid mono- and dialkanolamides according to the general structure

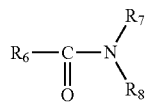

wherein $R_6$ is an alkyl chain which may be saturated or unsaturated, straight or branched, substituted or unsubstituted with a length of 8 to 22 C atoms, preferably 10 to 18 and more preferably 12 to 18 C atoms, $R_7$ and $R_8$ are same or different H, $C_1$ to $C_4$ alkyl or hydroxyl alkyl, preferably $C_2$ hydroxy alkyl with the condition that at least one of the $R_7$ and $R_8$ is not H.

Suitable non-limiting examples are behenoyl monoethanolamide, coco monoethanolamide, isostearoyl monoethanolamide, lauroyl monoethanolamide, myristoyl monoethanolamide, oleoyl monoethanolamide, ricinoleoyl monoethanolamide, stearoyl monoethanolamide, behenoyl diethanolamide, caproyl diethanolamide, cocoyl diethanolamide, isostearoyl diethanolamide, lauroyl diethanolamide, lineloyl monoethanolamide, myristoyl monoethanolamide, oleoyl monoethanolamide, palmitoyl diethanolamide, ricinoleoyl monoethanolamide and stearoyl monoethanolamide.

Further additionally useful non-ionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Another type of nonionic surfactants and the preferred ones are $C_{10}$-$C_{22}$-fatty alcohol ethoxylates. Especially suited are $C_{10}$-$C_{22}$-fatty alcohol ethers with the average degree of ethoxylation between 1 and 25, preferably 2 and 20, more preferably 2 to 10. Suitable examples are oleth-2, oleth-3, oleth-4, oleth-5, oleth-6, oleth-7, oleth-8, oleth-9, oleth-10, oleth-11, oleth-12, oleth-15, oleth-16, oleth-20, oleth-25, laureth-2, laureth-3, laureth-4, laureth-5, laureth-6, laureth-7, laureth-8, laureth-9, laureth-10, laureth-11, laureth-12, laureth-13, laureth-15, laureth-16, laureth-20, laureth-25, ceteth-10, ceteth-12, ceteth-14, ceteth-15, ceteth-16, ceteth-17, ceteth-20, ceteth-25, cetoleth-10, cetoleth-12, cetoleth-14, cetoleth-15, cetoleth-16, cetoleth-17, cetoleth-20, cetoleth-25, ceteareth-10, ceteareth-12, ceteareth-14, ceteareth-15, ceteareth-16, ceteareth-18, ceteareth-20, ceteareth-22, ceteareth-25, isosteareth-10, isosteareth-12, isosteareth-15, isosteareth-20, isosteareth-22, isosteareth-25, steareth-10, steareth-11, steareth-14, steareth-15, steareth-16, steareth-20, and steareth-25.

Further suitable and preferred non-ionic surfactants are glyceryl fatty acid esters according to the general formula

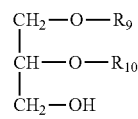

wherein $R_9$ and $R_{10}$ are same or different H, or a fatty acid group which may be saturated or unsaturated, branched or straight, substituted or unsubstituted with a C number between 10 and 22 with the condition at least one of the $R_9$ and $R_{10}$ is a fatty acyl group. The esters according the above general structure has preferably C number between 10 and 18 and more preferably 12 and 18.

Most preferred glyceryl fatty acid esters are glyceryl stearate and glyceryl distearate.

Further non-ionic surfactants within the meaning of the present invention are polyalkyleneglycol ether of fatty acid glyceride or partial glyceride with at least 20 polyalkylene units, especially with 20 to 150, more preferably 20 to 100, most preferably 30 to 75 polyethyleneglycol units. Examples to those are PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil, PEG-100 castor oil. Additional examples of similar compounds can be found in the cosmetic ingredient dictionaries and cosmetic textbooks.

Further suitable non-ionic surfactants within the meaning of present invention are glycol fatty acid esters according to the general structure

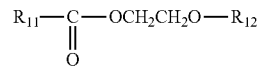

wherein $R_{11}$ is a saturated or unsaturated, branched or straight, substituted or unsubstituted alkyl with a 9 to 21C atoms and $R_{12}$ is H or a saturated or unsaturated, branched or straight, substituted or unsubstituted acyl with 10 to 22C atoms.

Suitable non-limiting examples are glycol ceteate, glycol dibehenate, glycol dilaurate, glycol dioleate, glycol stearate, glycol distearate, glycol oleate, glycol palmitate, glycol ricinoleate, and glycol stearate SE. Most preferred are glycol stearate SE, glycol stearate and glycol distearate.

Further suitable non-ionic surfactants are non-ionic silicone surfactants. Non-limiting suitable examples are PEG/PPG 3/10 dimethicone, PEG/PPG 4/12 dimethicone, PEG/PPG 6/4 dimethicone, PEG/PPG 6/11dimethicone, PEG/PPG 8/14 dimethicone, PEG/PPG 8/26 dimethicone, PEG/PPG 12/16 dimethicone, PEG/PPG 12/18 dimethicone, PEG/PPG 15/15 dimethicone, PEG/PPG 17/18 dimethicone, PEG/PPG 18/12 dimethicone, PEG/PPG 18/18 dimethicone, PEG/PPG 19/19 dimethicone, PEG/PPG 15/20 dimethicone, PEG/PPG 20/20 dimethicone, PEG/PPG 20/23 dimethicone, PEG/

PPG 20/29 dimethicone, PEG/PPG 22/23 dimethicone, PEG/PPG 22/24 dimethicone, PEG/PPG 25/25 dimethicone, PEG/PPG 27/27 dimethicone, PEG/PPG 20/29 dimethicone and PEG/PPG 20/29 dimethicone.

Among the non-ionic surfactants mentioned above alkyl polygulcosides, fatty alcohol ethoxylates, fatty acid mono and dialkanolamides and their mixtures at any weight ratio are the most preferred ones.

In a preferred form of the present invention, composition A and/or B comprises at least one fatty alcohol ethoxylate, at least one alkyl polyglucoside and at least one, fatty acid mono or dialkanolamide at any weight ratio. In a further preferred embodiment the surfactants are contained at a weight ratio of fatty alcohol ethoxylate:alkyl polyglucoside:fatty acid mono or dialkanolamide between 0.1:1:0.1 and 1:1:0.5, and preferably between 0.2:1:0.2 and 0.75:1:0.5.

In a further preferred embodiment, additionally composition A and/or B comprises at least one non-ionic silicone surfactant.

Nonlimiting suitable examples of anionic surfactants are the sulfate, sulfonate, carboxylate and alkyl phosphate type, especially, of course, those customarily used $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates and their salts.

Particular reference is made to the fatty alcohol ether sulfates of the general structure

$R_{14}(OCH_2CH_2)_nOSO_3M$

Wherein $R_{14}$ is a saturated or unsaturated, straight or branched, substituted or unsubstituted alkyl chain with 10 to 18C atoms, n is from 1 to 5 and M is a cation, preferably ammonium, sodium or potassium.

Suitable examples are ammonium capryleth sulphate, ammonium C12-15 pareth sulphate, ammonium laureth sulphate, ammonium laureth-5 sulphate, ammonium myreth sulphate, DEA C12-13 pareth-3 sulphate, DEA laureth sulphate, DEA myreth sulphate, diethylamine laureth sulphate, magnesium coceth sulphate, magnesium laureth sulphate, magnesium laureth-5 sulphate, magnesium myreth sulphate, magnesium oleth sulphate, MEA laureth sulphate, MIPA C12-15 pareth sulphate, MIPA laureth sulphate, sodium coceth sulphate, sodium C9-15 pareth-3 sulphate, sodium C10-15 pareth-3 sulphate, sodium C12-16 pareth-2 sulphate, sodium C12-13 pareth sulphate, sodium C12-14 pareth-3 sulphate, sodium C12-15 pareth sulphate, sodium C12-15 pareth-3 sulphate, sodium C13-15 pareth-3 sulphate, sodium doceth sulphate, sodium laneth sulphate, sodium laureth sulphate, sodium laureth-5 sulphate, sodium myreth sulphate, sodium oleth sulphate, TEA laureth sulphate, TEA laneth sulphate and TIPA laureth sulphate.

Among the anionic alkyl ether sulphate surfactants sodium laureth sulphate and its magnesium, TEA, MIPA salts are preferred.

Further anionic surfactants of the carboxylate type are alkyl polyether carboxylic acids and the salts thereof of the formula

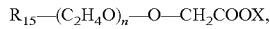
$R_{15}-(C_2H_4O)_n-O-CH_2COOX$, wherein $R_{15}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

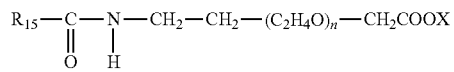

wherein $R_{15}$ and X have the above meanings, and n is in particular a number from 1 to 10, preferably 2.5 to 5.

Further suitable anionic surfactants are also $C_8$-$C_{22}$-acyl aminocarboxylic acids or the water-soluble salts thereof. Suitable ones are N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Among the anionic surfactants most preferred are alkyl sulfates and/or alkyl ether sulfates and among them sodium lauryl or laureth sulfates and their mixtures are most preferred.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

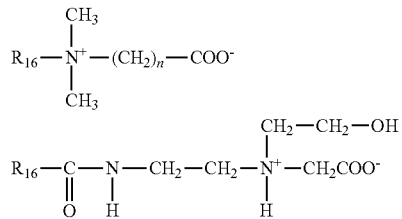

wherein $R_{16}$ is a $C_8$-$C_{18}$-alkyl group and n is 1 to 3; sulfobetaines of the structure

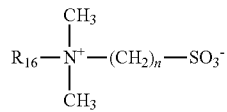

wherein $R_{16}$ and n are same as above; and amidoalkyl betaines of the structure

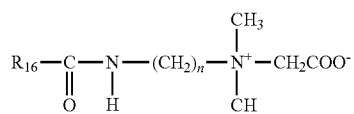

wherein $R_{16}$ and n are same as above.

Suitable nonlimiting examples are almondamidopropyl betaine, apricotamidopropyl betaine, avocadoamidopropyl betaine, babasuamidopropyl betaine, behenamidopropyl betaine, cocamidopropyl betaine, lauramidopropyl betaine, myristylamidopropyl betaine, oleamidopropyl betaine, olivamidopropyl betaine, palmamidopropyl betaine, palmitamidopropyl betaine, ricinoleamidopropyl betaine, sesamamidopropyl betaine, soyamidopropyl betaine, stearamidopropyl betaine, behenyl betaine, cetyl betaine, myristyl betaine, lauryl betaine, coco betaine, decyl betaine, oleyl betaine, stearyl betaine, tallow betaine, cocamidopropyl hydroxysultaine, coco hydroxysultaine, coco sultaine, lauramidopropyl hydroxysultaine, lauryl hydroxysultaine, myristamidopropyl hydroxysultaine, oleamidopropyl hydroxysultaine and lauryl sultaine Preferred amphoteric surfactants are of betaine types such as coco betaine and cocoylamidpropyl betaine.

In especially preferred from of the present invention, composition A and/or B comprise at least one non-ionic surfactant, preferably alkyl polyglucoside type, at least one anionic surfactant, preferably alkyl ether sulphate and at least one amphoteric surfactant, preferably alkyl betaine and/or alkyl amidoalkylbetaine type.

Composition A and/or B comprise one or more cationic and/or cationizable surfactants with the general formula

wherein $R_{17}$ is a saturated or unsaturated, straight or branched alkyl group with 8 to 24C atoms, $R_{18}$ is a straight or branched alkyl group with 1 to 4C atoms, A is a group selected from O,

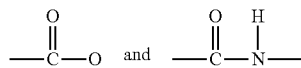

and B is selected from

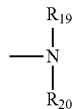

wherein $R_{19}$ and $R_{20}$ are the same or different is H or an alkyl with 1 to 4C atoms, hydroxyl alkyl with 1 to 4C atoms and di hydroxyl alkyl with 2 to 4C atoms,

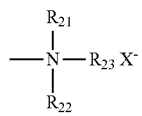

$R_{21}$, and $R_{22}$ are the same or different, an alkyl with 1 to 4C atoms, hydroxyl alkyl with 1 to 4C atoms and di hydroxyl alkyl with 2 to 4C atoms, $R_{23}$ is an alkyl with 1 to 4C atoms, hydroxyl alkyl with 1 to 4C atoms or di hydroxyl alkyl with 2 to 4C atoms and

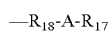

wherein $R_{17}$, A and $R_{18}$ have the above meaning and X is chloride, bromide, methosulfate, or a quaternary ammonium surfactant according to the general formula

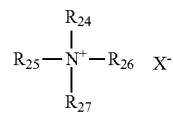

where $R2_4$ is a saturated or unsaturated, branched or non-branched alkyl chain with 8-24C atoms and $R_{25}$ is unsaturated or saturated, branched or non-branched alkyl chain with 1-24C atoms and $R_{26}$ and $R_{27}$ are lower alkyl chain with 1 to 4 carbon atoms which may be substituted with one or more hydroxyl groups, and X is anion such as chloride, bromide, methosulfate.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl methylamine, stearamidopropyl diethylamine, stearamidopropyl dibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, dicocoylethylhydroxyethylmonium methosulfate, cetyltrimethyl ammonium chloride, steartrimonium chloride, behentrimonium chloride, myristyltrimethyl ammonium chloride, distearyldimethyl ammonium chloride, and dibehenyldimethyl ammonium chloride.

In a preferred embodiment of the present invention, composition A and/or B comprises at least one fatty acid soap. In principal any fatty acid soap is suitable, however, preferred fatty acid soaps are sodium and potassium soaps. The fatty acid may be saturated or unsaturated, branched or straight and substituted or unsubstituted. Non-limiting suitable examples are soaps and especially sodium and/or potassium soaps of lauric acid, myristic acid, palmitic acid, palmitoleic acid, stearic acid, oleic acid, linoleic acid, linolenic acid, behenic acid, capric acid, caproic acid, caprylic acid, isostearic acid and ricinoleic acid as well as the ones obtained from native oils such as olive acid, corn acid, palm acid, rapeseed acid etc. Preferred are soaps of myristic acid, palmitic acid, palmitoleic acid, stearic acid, oleic acid, linoleic acid and ricinoleic acid and especially sodium and/or potassium soaps. More preferred are soaps of palmitoleic acid, oleic acid, linoleic acid and ricinoleic acid and the most preferred are soaps of oleic and linoleic acids.

Concentration of fatty acid soap varies between 0.1 and 20% preferably 0.2 and 15, more preferably 2 and 12.5 and most preferably 5 to 10% by weight calculated to the total of composition A or B.

Composition A and/or B may further comprise one or more fatty alcohol of the general formula

wherein $R_{13}$ is a linear or branched, saturated or unsaturated, substituted or unsubstitited alkyl chain with 12 to 22C atoms.

Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 0.1 to 5%, preferably 0.2 to 3.5%, more preferably 0.2 to 2.5% and most preferably 0.5 to 2% by weight calculated to total of composition A or B.

The composition A and/or B, and especially composition B comprises further hair-conditioning agents. Conditioning agents can be selected from oily substances, non-ionic substances, cationic and/or cationizable amphiphilic ingredients, cationic polymers, amphoteric polymers or their mixtures.

Oily substances are selected from such as silicone oils, either volatile or non-volatile, natural and synthetic oils. Among silicone oils those can be added to the compositions include dimethicone, dimethiconol, polydimethylsiloxane, DC fluid ranges from Dow Corning, as well as aminated silicones such as amodimethicone, aminopropyl phenyl trimethicone; arylated silicones with one to 5 phenyl groups in its molecule such as trimethylpentaphenyl trisiloxane, phenyl trimethicone, triphenly trimethicone and cyclic siloxanes such as cyclomethicone, cyclotrisiloxane, cyclopentasiloxane, cycloheptasiloxane and cyclotrisiloxane. Natural oils such as olive oil, almond oil, avocado oil, wheatgerm oil and ricinus oil can be included as conditioning agents in the composition A and/or B.

Synthetic oils can be included in composition A and/or B as conditioning agent such as mineral oil, alkyl esters of fatty acids such as isopropyl myristate, palmitate, stearate and isostearate, oleyl oleate, isocetyl stearate, hexyl laurate, dibutyl adipate, dioctyl adipate, myristyl myristate and oleyl erucate.

Further conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

or

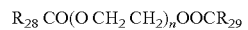

where $R_{28}$ and $R_{29}$ are independent from each other saturated, unsaturated or branched or non-branched alkyl chain with 7 to 21C atoms and n is typically 2-100.

Additionally composition A and/or B comprises one or more cationic polymers as conditioning agents. Suitable cationic polymers are those of known with their CTFA category name Polyquaternium. Typical examples of those Polyquaternium 6, Polyquaternium 7, Polyquaternium 10, Polyquaternium 11, Polyquaternium 16, Polyquaternium 28, Polyquaternium 70, Polyquaternium 67, and Polyquaternium 87. Preferred are Polyquaternium 6 and 7, polyquaternium 10 and especially polyquaternium-7.

The cationic polymers also include the quaternized products of graft polymers from organopolysiloxanes and polyethyl oxazolines described in EP-A 524 612 and EP-A 640 643.

Additionally, composition A and/or B comprises at least one amphoteric polymer. Non-limiting suitable and preferred examples are Polyquaterinium-22, Polyquaterinium-35, Polyquaterinium-39, Polyquaterinium-30 and Polyquaterinium-45. The more preferred are Polyquaterinium-39 and Polyquaterinium-22 and the most preferred is Poyquaternium-22.

In a particularly preferred embodiment of the present invention, composition A and/or B comprise at least one cationic polymer, at least one amphoteric polymer and at least one silicone compound as the conditioning agents.

The composition A and/or B according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Additional natural plant extracts can as well form part of the compositions A and/or B of the present invention. Those are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, green tea, blue lotus flower, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapone" products and "Herbasol®". Extracts and the preparation thereof are also described in "Hagers Handbuch der pharmazeutischen Praxis", $4^{th}$ Ed.

The composition B can comprise one or more organic solvents such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvent can be in the range of 1 to 10%, preferably 1 to 7.5% by weight, calculated to total of composition B.

Composition B can comprise UV filters for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof and/or 3-(4'-methyl benzylidene)-DL-campher, polysilicone-15. The preferred amount of the UV-absorber ranges from about 0.01% to 2.5%, more preferably from 0.05% to 1% by weight, calculated to the total of composition B.

It should be noted that for levelling hair colour within the meaning of the present invention, hair dyes are not required, especially when this is done on a previously partly or as a whole bleached hair.

On the other hand, in principal any kind of hair dye may be included in the compositions of the present invention.

One or more oxidative dye precursors can be comprised in composition B in case the leveling process is carried out on a lighter coloured hair. On the other hand, oxidative dye precursors may also be used if such leveling process is carried out for previously bleached hair depending on the target colour direction, warmer colours including more of golden and red tones as well as cooler tones including ash, matt and violet tones may require use of oxidative dye precursors. It should be noted that leveling is carried out in the absence and as well in the presence of oxidative dye precursors. Suitable oxidative dyestuffs precursors, if required, are tetraaminopyrimidines, in particular 2,4,5,6-tetraaminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof, aminophenol derivatives such as 4-aminophenol, 4-amino-3-methylphenol, 2-chloro-4-aminophenol, 2,6-dichloro-4-aminophenol, 2,4-diamino-phenol, 2,6-dibromo-4-aminophenol and/or 2-aminophenol and water-soluble salts thereof, furthermore, phenylenedimanine derivatives such as 2,5-diamino-toluene, 2-n-propyl or 2-ethyl-p-phenylene-diamine, 2,6-dimethyl-p-phenylenediamine, 2-(2,5-diaminophenyl)ethanol, 1-amino-4-bis-(2'-hydroxy-ethyl) aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethylamino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene or the water-soluble salts thereof, pyrazole derivatives such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, 1-methyl-3-phenyl-4,5-diaminopyrazole and the water-soluble salts. The use of the above mentioned oxidative dye precursors as mixture is also customary in hair coloring area.

The total concentration of the oxidation dyestuff precursors and/or their water soluble salts if required may vary between 0.0001% and 1%, preferably 0.001% and 1%, in particular 0.001% to 0.5% by weight, calculated to the total of composition B.

The composition B may as well comprise in addition to the oxidative dye precursors at least one coupling substance, which can be selected from resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2-methylamino-6-methoxypyridine, 2-amino-3-hydroxypyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. However, this shall not exclude the addition of further developing and coupling substances. In case oxidative dye precursors are used, preferably composition B comprises additionally at least one coupling agent.

The concentration of coupling substances is customarily adjusted to the concentration of developing, oxidative dye precursor, substances.

The composition B can further comprise additionally direct dyes of neutral, cationic and anionic character. Some examples to suitable cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14 and Basic Yellow 57. According to the invention, suitable cationic dyestuffs are in principal those any available on the market for cosmetic hair colouring applications. For this purpose, special reference is made to the PCT application WO 95/15144 of Ciba-Geigy AG. The content of the PCT application WO 95/15144 is by reference incorporated here.

Examples to suitable direct acting anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Some examples to those suitable neutral dyes (HC dyes), so called nitro dyes, are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of direct dyes in the composition B is in the range of 0.001 to 1%, preferably 0.002 to 0.75%, more preferably 0.005 to 0.5% by weight calculated to total of the composition B.

The composition A and/or B may further comprise an organopolysiloxane wherein at least one silicon atom is linked to an alkylene group having a hetero-atom, in particular a nitrogen atom, with a poly-(N-acyl alkyleneimine) units of the formula

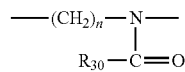

wherein n is a number from 1 to 5 and $R_{30}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

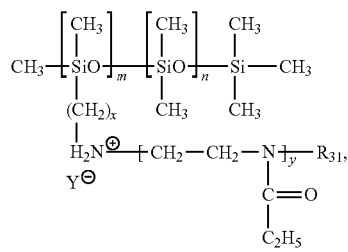

wherein m and n each are numbers from 20 to 10,000, in particular 50 to 7,000, especially 100 to 5,000, x is a number between 1 and 5, preferably 3, and y is a number from 5 to 30, $R_{31}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Another compound that may be comprised in composition A and/or B comprising is a ceramide according to the general formula

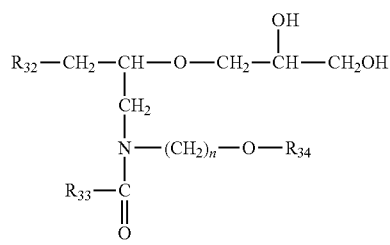

wherein $R_{32}$ and $R_{33}$ are independent from each other alkyl- or alkenyl group with 10 to 22 carbon atoms, $R_{34}$ is methyl, ethyl, n-propyl or isopropyl group and n is a number between 1 to 6, preferably 2 or 3. The concentration of the ceramide type of compound in colouring compositions of the present invention can be in the range of 0.01 to 2 and especially 0.01 to 1% by weight calculated to the total composition.

Preferred ceramide compound is cetyl-PG-hydroxyethylpalmitamide.

Sterols, especially the phytosterols, may as well be comprised in Composition B. Suitable ones are especially of plant origin for example ergosterol, sitosterol, stigmasterol, fucosterol, brassicasterol, fungisterol, campesterol, zymosterol, ascosterol, cerevisterol, episterol, faecosterol, spinasterol.

The concentration of ceramide may be in the range of 0.01 to 2% and phytosterol may be comprised in the range of 0.01 to 0.5% by weight calculated to the total of composition B.

The compositions A and/or B may further comprise one or more ubiquinone of the formula

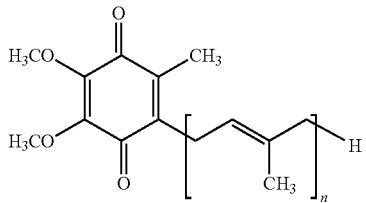

wherein n is a number from 1 to 10. The concentration of ubichinones in the compositions of the present invention can vary between 0.001% and 10% by weight, calculated to the total composition excluding the oxidizing agent.

The composition B of the present invention may comprise compounds for accelerating (catalysts) the oxidative dyeing keratin fibres such as iodine salts i.e. potassium or sodium iodide and/or dihydroxy acetone.

Further compositions A and/or B can comprise yogurt powder at a concentration of 0.01 to 5% by weight calculated to total of the compositions A or B, which is a raw material prepared by spray drying of natural yoghurt after completion of fermentation. Yogurt powder comprises the following major components:
- approximately 53.5% lactose,
- approximately 25% proteins,
- approximately 7.5% lactic acid,
- approximately 5% minerals and trace elements,
- approximately 1% vitamines, and
- approximately 2% lipids.

Composition A and/or B may comprise at least one diamide compound. Preferred diamide compounds are according to the general structure

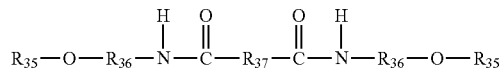

wherein $R_{35}$ is a linear or branched, saturated or unsaturated alkyl chain with 1 to 12 C atoms which may be substituted with hydroxy and/or alkoxy groups, preferably $R_{35}$ is linear or branched, saturated or unsaturated alkyl chain with 1 to 12C atoms which may be substituted by 1 to 3 substituents selected from a hydroxy group and C1 to C6 alkoxy group, more preferably $R_{35}$ is a unsubstituted alkyl group with 1 to 12C atoms, and alkyl group with 2 to 12C atoms substituted by one or two hydroxyl groups, by one alkoxy group with 1 to 6C atoms or by one hydroxyl and one alkoxy group with 2 to 6C atoms, $R_{36}$ is linear or branched alkyl chain with 1 to 5C atoms, preferably linear or branched alkyl chain with 2 to 5C atoms and more preferably an alkyl chain with 2 to 3C atoms, and $R_{37}$ linear or branched, saturated or unsaturated alkyl chain with 1 to 22C atoms, preferably linear or branched, saturated or unsaturated alkyl chain with 11 to 22C atoms.

Preferred individual diamide compounds are the ones according to the formula A to G.

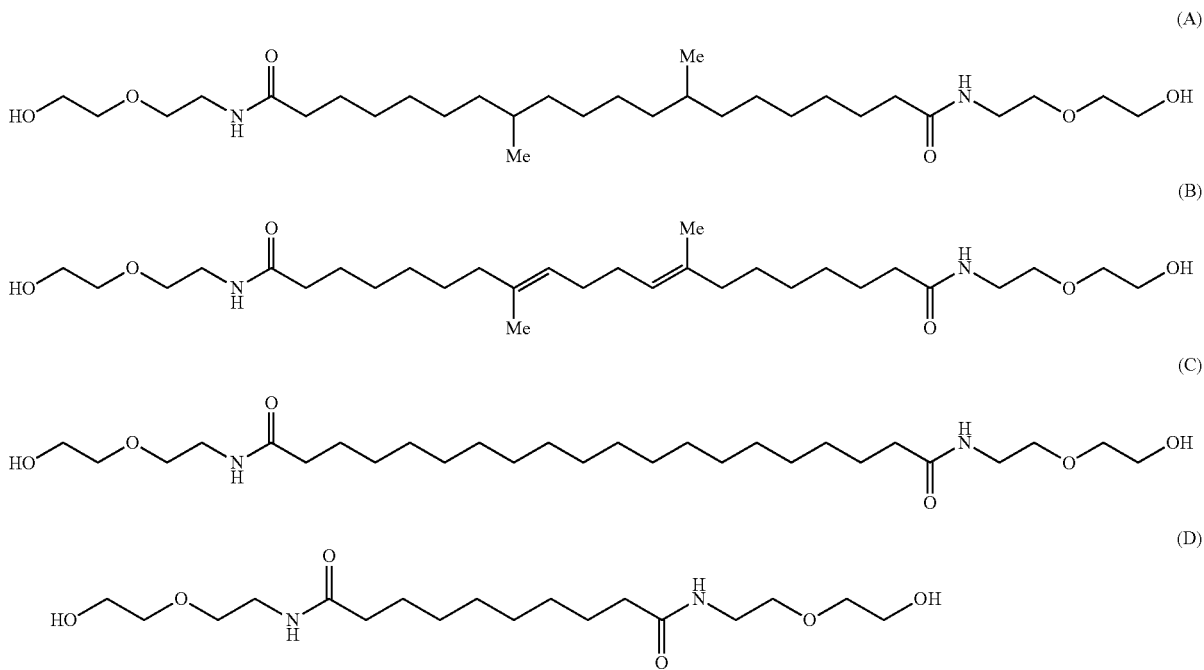

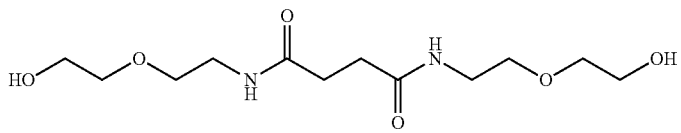

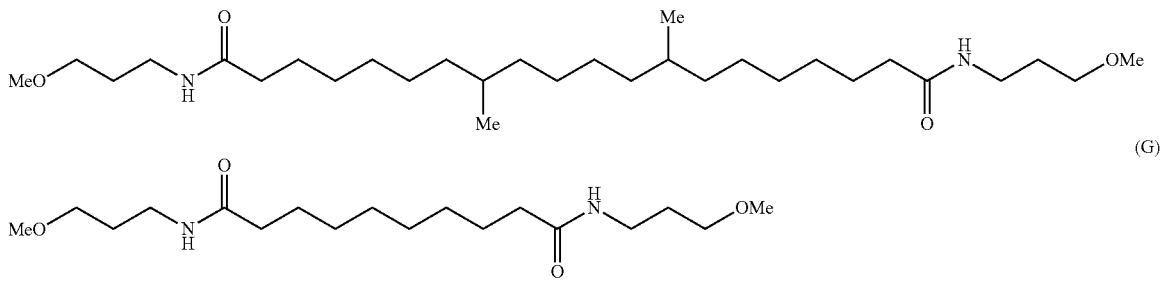

Particularly preferred diamide compound is the compound F which is bis(methoxypropylamido)isodocosane and commercially available from Kao Corporation—Japan.

Concentration of diamide compounds in the compositions A and/or B of the present invention is in the range of 0.001 to 5%, preferably 0.002 to 3% more preferably 0.005 to 2% and most preferably 0.01 to 1% by weight calculated to total of the compositions A or B.

Compositions A and/or B may further comprise particulate matter such as synthetic mica. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference.

Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and are known with their INCI names Synthetic Fluorphologopite.

The particle size distribution of synthetic mica coated with a metal oxide or oxides is in the range of 1 to 750 μm, preferably 1 to 250 μm, more preferably 1 to 100 μm and most preferably 20 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.25 to 2.5% by weight calculated to total of the compositions A or B.

Composition A and/or B may further comprise one or more dipeptide. Non-limiting examples to the suitable dipeptides are the ones commercially available and known with their INCI name as Dipeptide-1, Dipeptide-2, Dipeptide-3, Dipeptide-4, Dipeptide-5, Dipeptide-6, Dipeptide-7, Dipeptide-8, and carnosine. The most preferred is carnosine and is containing R-alanin and L-histidine.

Concentration of at least one dipeptide is in the range of 0.01 to 5%, preferably 0.05 to 3% and more preferably 0.1 to 2.5% and most preferably 0.2 to 1.5% by weight calculated to the total of the compositions A or B.

Composition A comprises at least one oxidizing agent, preferably at a concentration of at least 0.5% by weight calculated to total of composition A, preferably between 1 and 12% and more preferably 1 and 9% and most preferably 2 and 6% and in particular 2 to 3% by weight calculated to total of composition A.

In principal any oxidizing agent is suitable such as hydrogen peroxide, urea peroxide, melamine peroxide and perborate salts. The most preferred is hydrogen peroxide. Composition A can further comprise ingredients commonly used in compositions comprising oxidizing agents such as stabilizers for peroxide compounds such as phenacetin, salicylic acid, chelating agents such as etidronic acid, EDTA and/or their salts, organic or inorganic acids such as phosphoric acid, lactic acid, for adjusting pH, surfactants in order to increase miscibility and solubilising aid for water insoluble and/or sparingly soluble substances such as fragrances and anti-foaming agents such as silicone compounds.

Compositions A and B are mixed at a weight ratio of Composition A to Composition B in the range between 5:1 and 1:5, preferably between 3:1 and 1:3, more preferably between 2:1 and 1:2, and most preferably between 2:1 and 1:1. pH of the composition thus obtained and ready to use is in the range between 5 and 12, preferably between 6 and 11, more preferably between 6.5 and 11 most preferably between 8 and 10.5.

Any commercially available foamer vessels are suitable for the method of the present invention. Preferred are squeeze foamers which are disclosed in a published patent application EP 1 470 812 A1 and the disclosure is included herewith by reference.

It has further been found out that the viscosity of the composition resulting from mixing two compositions A and B is important for delivering the composition in the foam form. Therefore the mixture preferably has a viscosity in the range between 1 and 2000 mPa·s., preferably between 50 and 1500 mPa·s, more preferably between 50 and 1000 mPa·s., and most preferably between 100 and 750 mPa·s. measured at 20° C. with a rotation viscosimeter, preferably with a Brookfiled viscosimetre at 5 rpm with a spindle 5.

In order to achieve required viscosity in case it is necessary, inorganic salts are included in the composition A and/or B in case due to the high surfactant content viscosity is increased. Any monovalent inorganic slats are suitable for the purposes of the present invention. Preferred are sodium chloride, sodium carbonate and sodium bicarbonate. Concentration of the salt is in the range of 2 to 5% by weight calculated to total of composition A or B.

The following examples are to illustrate the invention but not limit it.

EXAMPLE 1

Composition A

|  | % by weight |
| --- | --- |
| Hydrogen peroxide | 3.0 |
| Sodium laureth sulphate | 0.5 |
| Phosphoric acid | q.s. to pH 3.0 |
| Phenacetin | 0.1 |
| EDTA | 0.3 |
| Water | q.s. to 100 |

Composition B

|  | % by weight |
| --- | --- |
| Decyl glucoside | 5.0 |
| Sodium laureth sulfate | 2.0 |
| Potassium oleate | 0.1 |
| Ammonium hydroxide | 4.0 |
| Water | q.s. to 100 |

The Composition B had a pH of 10.5

The above compositions A and B were mixed at a weight ratio of 2:1 (A:B) and the ready to use composition had a pH of 9.5.

The above composition was applied to the grown natural hair having a medium blonde colour after mixing as given above onto previously light blonde coloured hair from a squeeze foamer. The hair was coloured approximately 6 weeks before the current leveling process. After processing of 5 min the hair was rinsed of and dried with a hair drier.

It was observed that the hair colour was more homogeneous and the colour of the re-growth area was much closer. Additionally, volunteers, 5 people, were asked if they had any scalp problems during and also after the treatment, no negatives were mentioned. The same question was asked again 3 days after the leveling service and no complaints were noted.

Similar results were observed with the following examples.

EXAMPLE 2

Composition A

|  | % by weight |
| --- | --- |
| Hydrogen peroxide | 4.0 |
| Decyl glucoside | 1.0 |
| Phosphoric acid | q.s. to pH 3.0 |
| Phenacetin | 0.1 |
| EDTA | 0.3 |
| Water | q.s. to 100 |

Composition B

|  | % by weight |
| --- | --- |
| Decyl glucoside | 5.0 |
| Sodium laureth sulfate | 2.0 |
| Cocamidopropyl betaine | 2.0 |
| Dimethicone | 0.5 |
| Potassium oleate | 0.2 |
| Polyquaternium-7 | 0.2 |
| Polyquaternium-22 | 0.4 |
| Sodium chloride | 4.0 |
| Monoethanolamine | 4.0 |
| Water | q.s. to 100 |

The Composition B had a pH of 10.5

The above compositions A and B were mixed at a weight ratio of 1:1 (A:B) and the ready to use composition had a pH of 9.5.

EXAMPLE 3

Composition A

|  | % by weight |
| --- | --- |
| Hydrogen peroxide | 4.0 |
| Cetearyl alcohol | 1.0 |
| Ceteareth-20 | 0.5 |
| Phosphoric acid | q.s. to pH 3.0 |
| Phenacetin | 0.1 |
| EDTA | 0.3 |
| Water | q.s. to 100 |

Composition B

|  | % by weight |
| --- | --- |
| Decyl glucoside | 5.0 |
| Sodium laureth sulfate | 2.0 |
| Cocamidopropyl betaine | 2.0 |
| Dimethicone | 0.5 |
| Polyquaternium-7 | 0.2 |
| Polyquaternium-22 | 0.4 |
| Potassium oleate | 0.2 |
| Sodium chloride | 4.0 |
| p-Toluenediamine sulfate | 0.06 |
| Resorcinol | 0.01 |
| m-Aminophenol | 0.01 |
| HC Blue 5 | 0.01 |
| Sodium sulfit | 0.3 |
| Monoethanolamine | 4.2 |
| Water | q.s. to 100 |

The Composition B had a pH of 10.5

The above compositions A and B were mixed at a weight ratio of 1:1 (A:B) and the ready to use composition had a pH of 9.7.

EXAMPLE 4

Composition A

|  | % by weight |
| --- | --- |
| Hydrogen peroxide | 4.0 |
| Cetearyl alcohol | 1.0 |
| Ceteareth-20 | 0.5 |
| Phosphoric acid | q.s. to pH 3.0 |
| Phenacetin | 0.1 |
| EDTA | 0.3 |
| Water | q.s. to 100 |

Composition B

|  | % by weight |
| --- | --- |
| Decyl glucoside | 5.0 |
| Sodium laureth sulfate | 2.0 |
| Cocamidopropyl betaine | 2.0 |
| Polyquaternium-7 | 0.2 |
| Polyquaternium-22 | 0.4 |
| Potassium oleate | 0.2 |
| Sodium chloride | 4.0 |
| Basic red 51 | 0.06 |
| Basic orange 31 | 0.01 |
| Basic yellow 87 | 0.01 |
| HC Blue 5 | 0.01 |
| Monoethanolamine | 4.2 |
| Water | q.s. to 100 |

The Composition B had a pH of 10.5

The above compositions A and B were mixed at a weight ratio of 1:1 (A:B) and the ready to use composition had a pH of 9.7.

The invention claimed is:

1. A method of levelling colour of hair comprising at least two parts wherein one part being the part not closer to scalp which is artificially colour changed to a lighter colour by means of lightening and/or colouring and/or bleaching than the other part closer to scalp which is undamaged and has its natural colour, wherein hair is optionally shampooed and optionally towel dried and the part directly at the scalp is applied a composition resulting from mixing two compositions, A and B, prior to application, compositions A is aqueous composition and comprises at least one oxidizing agent and has an acidic pH, and composition B is an aqueous alkaline composition and has a pH between 8 and 12, wherein compositions A and/or B comprise at least one surfactant selected from non-ionic, anionic, amphoteric, cationic or cationizable ones, from a non-aerosol foamer vessel in the form of a foam and processed for up to 10 min, at a temperature between 20 and 45° C., and rinsed off from hair and hair is optionally dried.

2. The method according to claim 1, wherein composition B comprises as an alkalizing agent ammonia and/or carbonate salts and/or bicarbonate salts and/or substituted amine compound according to general structure $R_1R_2R_3N$ wherein $R_1$, $R_2$ and $R_3$ are same or different H, $C_1$-$C_6$ alkyl, $C_1$-$C_6$ monohydroxyalkyl or $C_2$-$C_6$ polyhydroxyalkyl with the condition that at least one of $R_1$, $R_2$ and $R_3$ is a mono or polyhydroxyalkyl, at a concentration between 1 and 20% by weight calculated to total of Composition B.

3. The method according to claim 1, wherein composition A and/or B comprises at least one non-ionic surfactant, at least one anionic surfactant of alkyl ether sulphate type and at least one amphoteric surfactants.

4. The method according to claim 1, wherein composition A and/or B comprises at least one fatty acid soap.

5. The method according to claim 1, wherein surfactants are comprised in compositions A and/or B at a concentration of 0.5 and 15% by weight calculated to total of composition A or B.

6. The method according to claim 1, wherein composition A and/or B comprises at least one fatty alcohol.

7. The method according to claim 1, wherein compositions A and/or B comprises at least one cationic polymer.

8. The method according to claim 1, wherein compositions A and/or B comprises at least one amphoteric polymer.

9. The method according to claim 1, wherein composition B comprises at least one inorganic salt at a concentration between 2 and 5% by weight calculated to total of composition B.

10. The method according to claim 1, wherein composition B comprises at least one oxidative dye precursor, optionally at least one coupling substance and optionally at least one direct dye.

11. The method according to claim 1, wherein compositions A and B are mixed at a weight ratio of 5:1 to 1:5 and the mixture has a pH between 5 and 12.

12. The method according to claim 1, wherein compositions A and/or B comprises at least one compound selected from diamide compounds, ceramides, sterols, ubichinones, yoghurt powder, dipeptide and synthetic mica coated with metal oxide or oxides.

13. The method according to claim 1, wherein composition B comprises organic solvent and/or UV filter.

14. The method according to claim 1, wherein composition A comprises hydrogen peroxide as an oxidizing agent at a concentration between 0.5 and 12% by weight calculated to total of composition A.

* * * * *

UNITED STATES PATENT AND TRADEMARK OFFICE
CERTIFICATE OF CORRECTION

| | | |
|---|---|---|
| PATENT NO. | : 8,388,699 B2 | Page 1 of 1 |
| APPLICATION NO. | : 13/384940 | |
| DATED | : March 5, 2013 | |
| INVENTOR(S) | : Wood et al. | |

It is certified that error appears in the above-identified patent and that said Letters Patent is hereby corrected as shown below:

In the Specification

Column 10, lines 66-67, "Poyquaternium-22" -- should read -- Polyquaterinium-22 --.

Column 17, line 63, "R-alanin" -- should read -- β-alanin --.

Column 18, line 66, "slats" -- should read -- salts --.

Signed and Sealed this
Fifth Day of August, 2014

Michelle K. Lee
*Deputy Director of the United States Patent and Trademark Office*